(12) United States Patent
Kanno (10) Patent No.: US 10,070,773 B2
(45) Date of Patent: Sep. 11, 2018

(54) CONNECTION STRUCTURE AND MEDICAL DEVICE

(71) Applicant: Sony Olympus Medical Solutions Inc., Tokyo (JP)

(72) Inventor: Kiyotaka Kanno, Saitama (JP)

(73) Assignee: Sony Olympus Medical Solutions Inc., Tokyo (JP)

( * ) Notice: Subject to any disclaimer, the term of this patent is extended or adjusted under 35 U.S.C. 154(b) by 0 days.

(21) Appl. No.: 15/517,428

(22) PCT Filed: Oct. 27, 2015

(86) PCT No.: PCT/JP2015/080193
§ 371 (c)(1),
(2) Date: Apr. 6, 2017

(87) PCT Pub. No.: WO2016/088473
PCT Pub. Date: Jun. 9, 2016

(65) Prior Publication Data
US 2017/0296039 A1 Oct. 19, 2017

(30) Foreign Application Priority Data
Dec. 1, 2014 (JP) .................................. 2014-243526

(51) Int. Cl.
*H01R 13/68* (2011.01)
*A61B 1/00* (2006.01)
*H01R 13/62* (2006.01)

(52) U.S. Cl.
CPC ...... *A61B 1/00124* (2013.01); *A61B 1/00126* (2013.01); *H01R 13/6205* (2013.01); *H01R 2201/12* (2013.01)

(58) Field of Classification Search
CPC .............................................. H01R 13/6596
(Continued)

(56) References Cited

U.S. PATENT DOCUMENTS 3,371,147 A * 2/1968 Daubenberger ..... H05K 9/0018
174/358
6,529,087 B2 * 3/2003 Kawato ............... H05K 9/0018
333/12

(Continued)

FOREIGN PATENT DOCUMENTS

DE 25 03 033 7/1976
JP 11-337839 A 12/1999

(Continued)

OTHER PUBLICATIONS

International Search Report dated Jan. 26, 2016 in PCT/JP2015/080193 filed Oct. 27, 2015.

(Continued)

*Primary Examiner* — Phuong Dinh
(74) *Attorney, Agent, or Firm* — Oblon, McClelland, Maier & Neustadt, L.L.P.

(57) ABSTRACT

In a medical device that includes a tip-side device to be brought into contact with or inserted into an object to be observed and a root end-side device connected to the tip-side device, the leakage of radiation noise generated in the root end-side device to the outside and the entry of disturbance noise into the root end-side device are prevented. A connection structure includes a plug provided at a root end of a tip-side device, and a receptacle provided in the root end-side device and configured to hold the plug by insertion. At least one of the plug and the receptacle contains an electrically non-conductive magnetic material in a portion crossing an opening formed in the outer casing in a state where the plug is inserted in the receptacle.

11 Claims, 5 Drawing Sheets

(58) Field of Classification Search
USPC ........ 439/607.28, 607.27; 174/391, 390, 360
See application file for complete search history.

(56) References Cited

U.S. PATENT DOCUMENTS

| | | |
|---|---|---|
| 2001/0044227 A1 | 11/2001 | Boutros et al. |
| 2004/0092793 A1 | 5/2004 | Akai |
| 2014/0184771 A1 | 7/2014 | Mazzetti et al. |
| 2014/0309495 A1 | 10/2014 | Kirma et al. |

FOREIGN PATENT DOCUMENTS

| | | |
|---|---|---|
| JP | 2003-511815 A | 3/2003 |
| JP | 2003-204931 A | 7/2003 |
| JP | 2004-148028 A | 5/2004 |
| JP | 2013-13494 A | 1/2013 |

OTHER PUBLICATIONS

Extended European Search Report dated May 23, 2018 for European Patent Application No. 15865226.3.
Office Action dated Jun. 5, 2018 in Chinese Patent Application No. 2015800642627 (with English translation).

\* cited by examiner

CONNECTION STRUCTURE AND MEDICAL DEVICE

TECHNICAL FIELD

The present disclosure relates to a connection structure that connects a tip-side device and a root end-side device included in a medical device, and a medical device including the connection structure.

BACKGROUND ART

Thus far, in a medical device such as an endoscope system that is inserted into the interior of an object to be observed and acquires an image of the interior of a body, various measures are taken in order to remove noise leaking from the inside to the outside of the device. For example, Patent Literature 1 below discloses a technology in which an electrical shield is provided on the outer periphery of a cable that connects an endoscope (a tip-side device), and a processor and a light source device (root end-side devices) of an endoscope system and, in a root unit of a cable connector, a plurality of ferrite cores having different impedance characteristics to noise frequency are arranged on the outer peripheral side of an electrical shield body. The leakage of noise generated in the endoscope to the outside can be prevented by the technology described in Patent Literature 1.

CITATION LIST

Patent Literature

Patent Literature 1: JP H11-337839A

DISCLOSURE OF INVENTION

Technical Problem

In the case of the medical device described above, it is necessary to electrically insulate a patient circuit included in the tip-side device on the side of being brought into contact with or inserted into the object to be observed and a ground-side circuit that is included in the root end-side device and is grounded by functional grounding, protective grounding for ensuring the safety of the manipulator of the medical device, or the like, such as the primary circuit and the secondary circuit. Hence, in the medical device described above, it is necessary to ensure a spatial distance and a creeping distance for insulation between the tip-side device and the root end-side device. When a spatial distance and a creeping distance are ensured between the tip-side device and the root end-side device, there has been a fear that radiation noise generated in the root end-side device will leak from the gap between both devices to the outside or that disturbance noise will enter the interior of the root end-side device.

The present disclosure has been made in view of the above, and an object of the present disclosure is to provide a connection structure that, in a medical device that includes a tip-side device to be brought into contact with or inserted into an object to be observed and a root end-side device connected to the tip-side device, can prevent the leakage of radiation noise generated in the root end-side device to the outside and the entry of disturbance noise into the root end-side device, and a medical device including the connection structure.

Solution to Problem

In order to solve the above problem and achieve the object, a connection structure for connecting a tip-side device and a root end-side device of a medical device, the medical device including the tip-side device configured to be brought into contact with or inserted into an object to be observed, and the root end-side device connected to the tip-side device and including a grounded outer casing, includes: a plug provided at a root end of the tip-side device; and a receptacle provided in the root end-side device and configured to hold the plug by insertion. At least one of the plug and the receptacle contains an electrically non-conductive magnetic material in a portion crossing an opening formed in the outer casing in a state where the plug is inserted in the receptacle.

In the connection structure, the magnetic material may be provided in an outer casing of the plug.

In the connection structure, the magnetic material may be provided on an inner peripheral side with respect to an outer casing of the plug.

In the connection structure, the magnetic material may be provided in the receptacle.

A medical device according to the present disclosure includes the connection structure mentioned above.

In the medical device, the tip-side device may be an endoscope configured to be inserted into the object to be observed and acquire information of the object to be observed, and the root end-side device may be a control device configured to control the tip-side device and process information received from the tip-side device and/or a light source device configured to generate illumination light that the tip-side device applies to the object to be observed.

Advantageous Effects of Invention

According to the present disclosure, at least one of a plug and a receptacle contains an electrically non-conductive magnetic material in a portion crossing an opening formed in an outer casing of the root end-side device in a state where the plug is inserted in the receptacle, and thus a spatial distance and a creeping distance are ensured by filling the gap between the tip-side device and the root end-side device with the magnetic material. Therefore, the leakage of radiation noise generated in the root end-side device to the outside and the entry of disturbance noise into the root end-side device can be prevented.

MODE(S) FOR CARRYING OUT THE INVENTION

Hereinbelow, embodiments of the present disclosure (hereinafter, referred to as "embodiments") are described with reference to the appended drawings. The drawings are only schematic ones, and portions for which the relationships between dimensions and the proportions are different among drawings may be included in the drawings.

Figure 1:
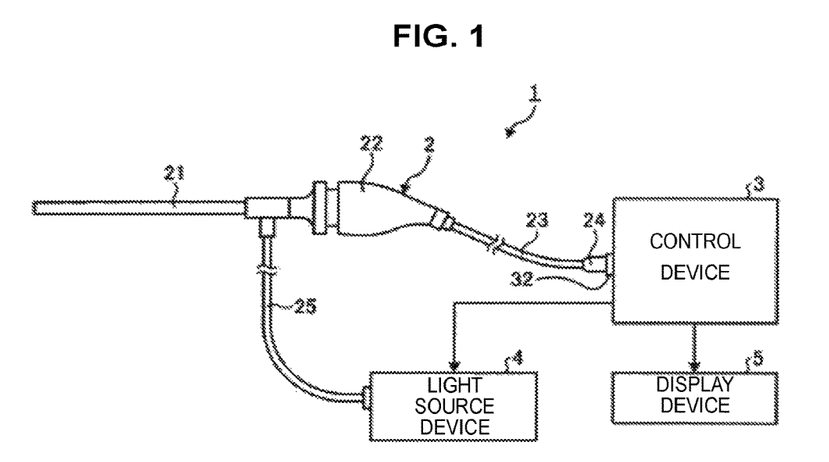
FIG. 1 is a diagram showing a rough configuration of an endoscope system that is a medical device according to an embodiment of the present disclosure.

FIG. 1 is a diagram showing a rough configuration of an endoscope system that is a medical device according to an embodiment of the present disclosure. An endoscope system 1 shown in the drawing includes an endoscope 2 as a tip-side device that captures an image of the interior of an object to be observed by inserting its tip into the interior of the object to be observed, a control device 3 as a root end-side device that is connected to the endoscope 2, and performs a prescribed image processing on an image of the interior of a body captured by the endoscope 2 to create image data for display and comprehensively controls the operation of the entire endoscope system 1, a light source device 4 that generates illumination light that is applied to the object to be observed from the tip of the endoscope 2, and a display device 5 that includes a liquid crystal display panel or an organic electro-luminescence (EL) display panel and displays an image.

The endoscope 2 includes an insertion unit 21 that is rigid and has a long, thin shape and of which the tip is inserted into the interior of the object to be observed, a camera head 22 that is connected to the root end of the insertion unit 21 in an attachable and detachable manner, and captures an image of the object to be observed optically collected via the insertion unit 21 and outputs an imaging signal, a cable 23 that transmits an imaging signal outputted by the camera head 22 to the control device 3, a plug 24 that is a male connector that is provided at the root end of the cable 23 and is mounted on the control device 3 in an attachable and detachable manner, and a light guide 25 that transmits the illumination light generated by the light source device 4 to the tip of the insertion unit 21.

The insertion unit 21 includes a light collection optical system that is provided inside an outer casing having a cylindrical shape and collects light from the object to be observed and an illumination optical system that is provided inside the outer casing and applies the illumination light transmitted from the light source device 4 via the light guide 25 to the object to be observed. The light collection optical system and the illumination optical system are each configured using one or a plurality of lenses.

The camera head 22 includes an imaging element that photoelectrically converts the light collected by the optical system of the insertion unit 21 to generate an imaging signal and an input unit that accepts the input of an operation instruction signal of the endoscope 2. The imaging element is configured using an image sensor such as a charge-coupled device (CCD) or a complementary metal oxide semiconductor (CMOS).

Figure 2:
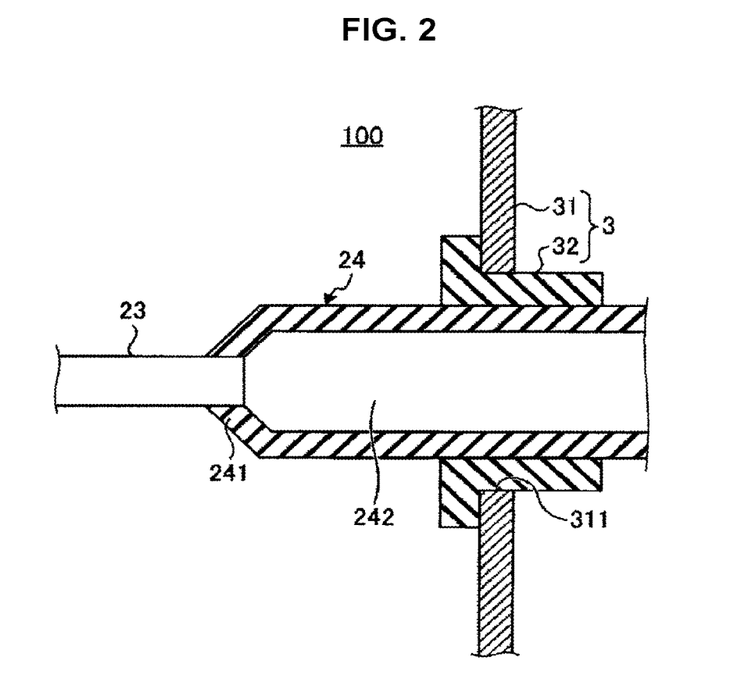
FIG. 2 is a partial cross-sectional view schematically showing the configuration of a main part of a connection structure according to an embodiment of the present disclosure.

The configuration of a main part of the plug 24 will now be described with reference to the partial cross-sectional view shown in FIG. 2. FIG. 2 is a partial cross-sectional view showing a state in which the plug 24 is inserted in a receptacle 32 (described later) that is a female connector included in the control device 3. As shown in FIG. 2, the plug 24 includes an outer casing 241 formed using an electrically non-conductive magnetic material and a shield body 242 made of a metal that is provided in the interior of the plug on the inner peripheral side of the outer casing 241 and has a cylindrical shape, receives the tip of the cable 23, and is connected to the reference potential of a patient circuit included in the endoscope 2 (the patient ground). In the state shown in FIG. 2, the outer casing 241 of the plug 24 crosses an opening 311 formed in a main body unit 31 of the control device 3.

As a specific material of the outer casing 241, a material obtained by a process in which a powder of a magnetic material such as ferrite, neodymium, or samarium cobalt is mixed with any of various electrically non-conductive resins, such as a polyamide (nylon) and polyphenylene sulfide, and the resulting material is molded by injection molding or is processed into a plate-like shape, a circular cylindrical shape, etc. may be used. It is also possible to use a material obtained by kneading a powder of a magnetic material such as ferrite, neodymium, or samarium cobalt with an electrically non-conductive rubber. Further, as an example in which a magnetic material itself is an electrically non-conductive plastic, a non-metal magnet made of a magnetic polymer (PANiCNQ) in which the skeleton of a polyaniline (PANi) in the emeraldine base form is provided with the structure of tetracyanoquinodimethane (TCNQ), which is an electron acceptor, is known and may be used. Also a configuration in which a magnetic material itself such as ferrite, neodymium, or samarium cobalt is used and a configuration in which a magnetic material is buried in part of an outer casing 241 formed of an electrically non-conductive resin may be used. In the case where a magnetic material itself is used as the outer casing 241, it goes without saying that the magnetic material itself needs to have electrical non-conductivity.

The outer casing 241 is preferably formed using a material having a high magnetic permeability in a wide band; for example, it is preferable to use a material having a magnetic permeability of 100 H/m or more in the range of 30 MHz or more. The material of the outer casing 241 is not limited to those described above, and a material that is adapted to the environment used and that does not give the influence of noise to a peripheral device used in combination with the endoscope 2 and is free from the influence of noise from the peripheral device may be set as appropriate.

The control device 3 includes a main body unit 31 having a casing shape and a receptacle 32 that is a female connector in a cylindrical shape that is attached to an opening 311 of the main body unit 31 and holds the plug 24 by insertion in an attachable and detachable manner. As shown in FIG. 2, the receptacle 32 crosses the opening 311 of the main body unit 31 of the control device 3.

The main body unit 31 is formed using a metal or an alloy. The main body unit 31 has a function as an outer casing (an outer shield) grounded at the reference potential of a ground-side circuit such as the secondary circuit included in the control device 3 (for example, the secondary ground) in order to provide electrical insulation from a patient circuit and ensure the safety of the object to be observed, the function of the endoscope system 1, and the manipulator. A front panel formed using a resin or the like may be provided on the outer surface of the main body unit 31.

The receptacle 32 is, similarly to the outer casing 241 of the plug 24, formed using an electrically non-conductive magnetic material. The receptacle 32 electrically connects a patient circuit of the endoscope 2 and a patient circuit provided in the control device 3. The patient circuit provided in the control device 3 is electrically insulated from the ground-side circuit such as the secondary circuit provided in the control device 3. The receptacle 32, together with the plug 24 of the endoscope 2, constitutes a connection structure 100 according to the embodiment (see FIG. 2).

The control device 3 is called also a processor, and has the function of performing a prescribed signal processing on an imaging signal generated by the endoscope 2 to create image data of the object to be observed. The control device 3 having such a function is configured using a central processing unit (CPU) etc.

In the one embodiment of the present disclosure described above, the plug 24 and the receptacle 32 contain an electrically non-conductive magnetic material in a portion crossing the opening 311 formed in the main body unit 31 of the control device 3 in a state where the plug 24 is inserted in the receptacle 32, and the gap of the connection portion between the endoscope 2 and the control device 3 is filled with the magnetic material; thereby, a spatial distance and a creeping distance between the endoscope 2 and the control device 3 are ensured. Therefore, by the embodiment, the leakage of radiation noise generated in the control device 3 to the outside and the entry of disturbance noise into the control device 3 can be prevented.

Furthermore, in the embodiment, since the leakage of radiation noise generated in the control device 3 to the outside and the entry of disturbance noise into the control device 3 are prevented by using an electrically non-conductive magnetic material as the material of the plug 24 and the receptacle 32, a shield in the connection portion between the plug 24 and the receptacle 32 can be obtained without complicating the configuration.

In the embodiment, it is sufficient that the electrically non-conductive magnetic material be provided at least in a portion of the outer casing 241 of the plug 24 and the receptacle 32 crossing the opening 311 of the main body unit 31 in a state where the plug 24 is inserted in the receptacle 32.

Although the case where the endoscope 2 is a rigid endoscope is described in the embodiment, also a flexible endoscope or an ultrasonic endoscope may be used as the endoscope.

Figure 3:
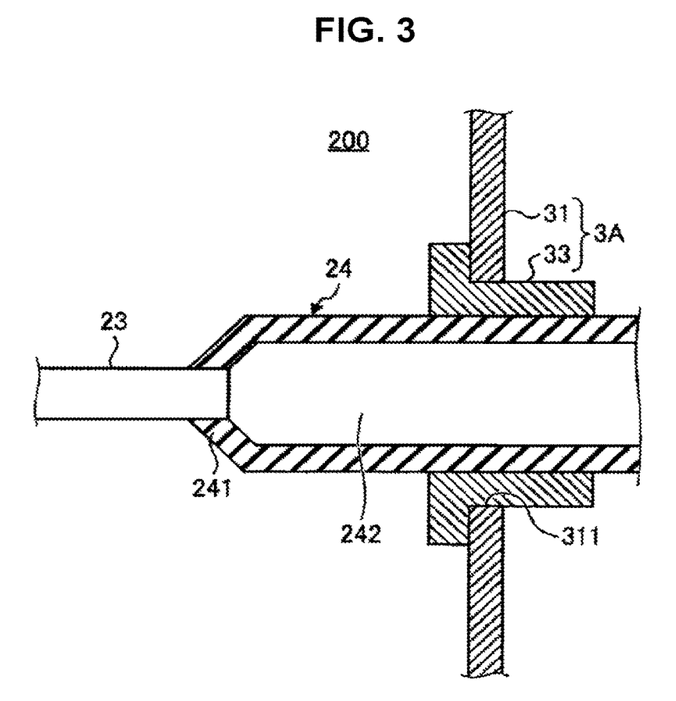
FIG. 3 is a partial cross-sectional view schematically showing the configuration of a main part of a connection structure according to Modification Example 1 of an embodiment of the present disclosure.

FIG. 3 is a partial cross-sectional view showing the configuration of a main part of a connection structure according to Modification Example 1 of the embodiment. In a connection structure 200 shown in the drawing, at least part of a receptacle 33 included in a control device 3A is formed using a metal or an alloy. The portion formed using a metal or an alloy preferably includes, for example, a portion where the receptacle 33 slides on the outer casing 241 when the plug 24 is inserted into the receptacle 33, or the like, and may be the entire receptacle 33. In the connection structure 200, only the outer casing 241 of the plug 24 is formed using an electrically non-conductive magnetic material. The configuration of the connection structure 200 other than the receptacle 33 is similar to the configuration of the connection structure 100. In the Modification Example 1, since the outer casing 241 containing an electrically non-conductive magnetic material is located in a portion crossing the opening 311 of the main body unit 31, effects similar to the above embodiment can be obtained. Furthermore, by the Modification Example 1, the abrasion resistance of the sliding portion to which the plug 24 of the endoscope 2, which is one of various tip-side devices, is connected can be improved.

Figure 4:
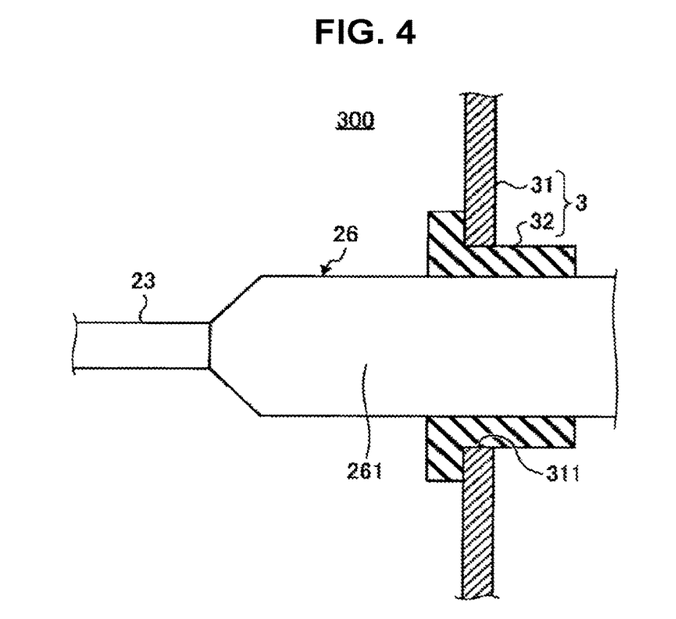
FIG. 4 is a partial cross-sectional view schematically showing the configuration of a main part of a connection structure according to Modification Example 2 of an embodiment of the present disclosure.

FIG. 4 is a partial cross-sectional view showing the configuration of a main part of a connection structure according to Modification Example 2 of the embodiment. In a connection structure 300 shown in the drawing, at least part of an outer casing 261 of a plug 26 is formed using a metal or an alloy connected to the patient ground. The portion formed using a metal or an alloy preferably includes, for example, a portion that slides on the receptacle 32 when the plug 26 is inserted into the receptacle 32, or the like, and may be the entire outer casing 261. In the connection structure 300, only the receptacle 32 is formed using an electrically non-conductive magnetic material. The configuration of the connection structure 300 other than the plug 26 is similar to the configuration of the connection structure 100. In the Modification Example 2, since the receptacle 32 containing an electrically non-conductive magnetic material is located in a portion crossing the opening 311 of the main body unit 31, similar effects to the above embodiment can be obtained.

Figure 5:
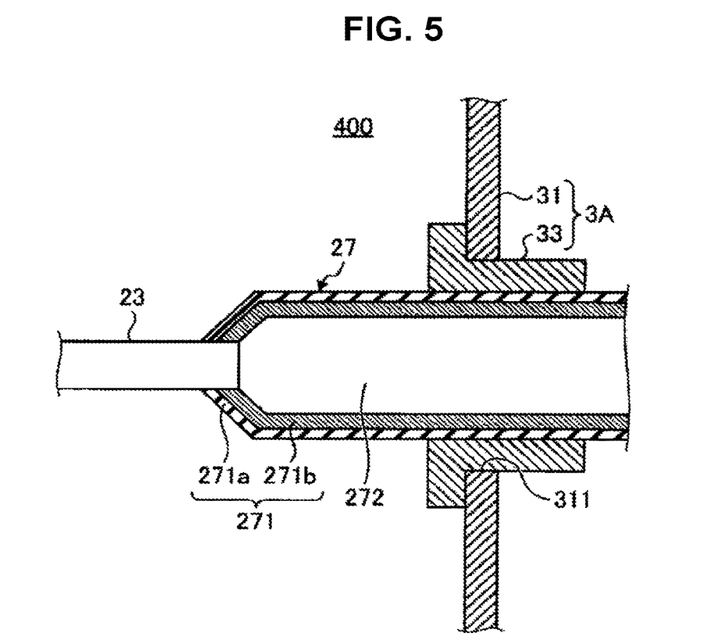
FIG. 5 is a partial cross-sectional view schematically showing the configuration of a main part of a connection structure according to Modification Example 3 of an embodiment of the present disclosure.

FIG. 5 is a partial cross-sectional view showing the configuration of a main part of a connection structure according to Modification Example 3 of the embodiment. A plug 27 included in a connection structure 400 shown in the drawing includes an outer casing 271 formed using an electrically non-conductive magnetic material and a shield body 272 made of a metal that is provided in the interior of the plug on the inner peripheral side of the outer casing 271 and has a cylindrical shape, receives the tip of the cable 23, and is connected to the patient ground. The outer casing 271 has an outer peripheral portion 271a formed using an electrically non-conductive magnetic material and an inner peripheral portion 271b that is stacked on the inner peripheral side of the outer peripheral portion 271a and is formed using a material other than the magnetic material mentioned above. The outer casing 271 is fabricated by, for example, applying an electrically non-conductive magnetic material to the surface of the inner peripheral portion 271b to form the outer peripheral portion 271a. The configuration of the connection structure 400 other than the plug 27 is similar to the configuration of the connection structure 200. In the Modification Example 3, since the outer peripheral portion 271a containing an electrically non-conductive magnetic material is located in a portion crossing the opening 311 of the main body unit 31, similar effects to the above embodiment can be obtained. It is also possible to provide an electrically non-conductive magnetic material in an inner peripheral portion of the outer casing of the plug.

Figure 6:
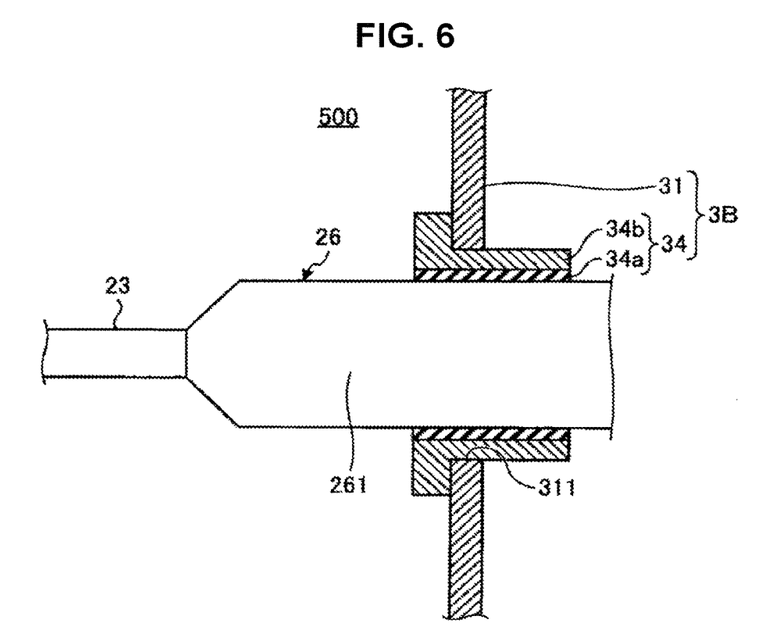
FIG. 6 is a partial cross-sectional view schematically showing the configuration of a main part of a connection structure according to Modification Example 4 of an embodiment of the present disclosure.

FIG. 6 is a partial cross-sectional view showing the configuration of a main part of a connection structure according to Modification Example 4 of the embodiment. A receptacle 34 included in a connection structure 500 shown in the drawing is attached to the opening 311 of the main body unit 31 of a control device 3B. The receptacle 34 has an inner peripheral portion 34a that is formed using an electrically non-conductive magnetic material and faces the plug 26 and an outer peripheral portion 34b that is formed using a material other than the magnetic material mentioned above and is located on the outer peripheral side of the inner peripheral portion 34a. The receptacle 34 is fabricated by, for example, applying an electrically non-conductive magnetic material to the surface on the inner peripheral side of an outer peripheral portion 34b having a cylindrical shape. In the Modification Example 4, since the inner peripheral portion 34a containing an electrically non-conductive magnetic material is located in a portion crossing the opening 311 of the main body unit 31, similar effects to the above embodiment can be obtained. It is also possible to provide an electrically non-conductive magnetic material in an outer peripheral portion of the receptacle.

Figure 7:
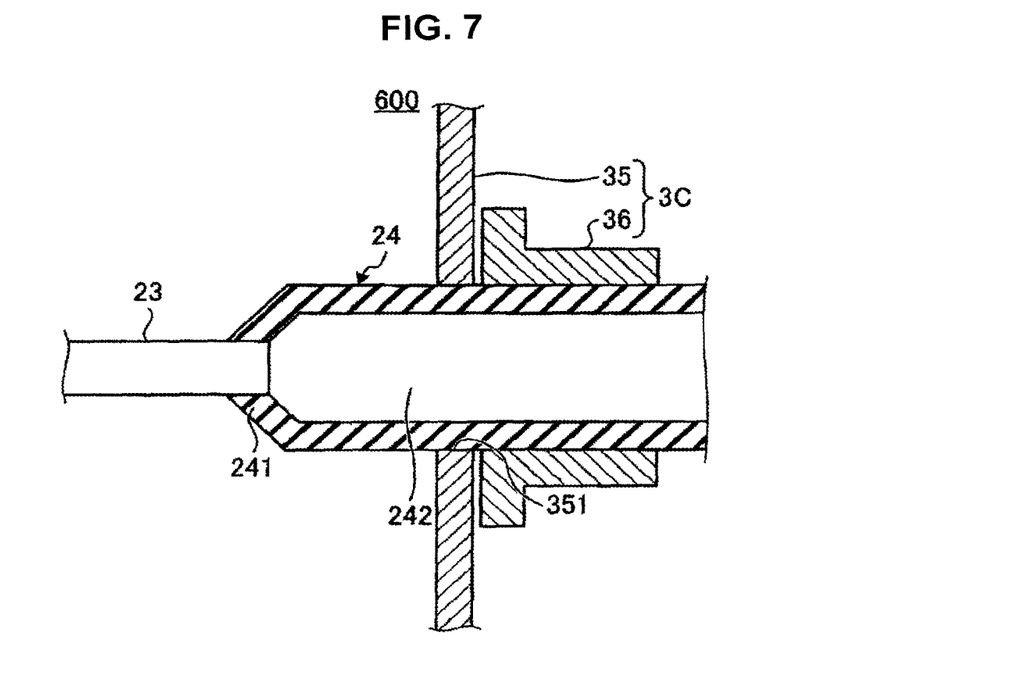
FIG. 7 is a partial cross-sectional view schematically showing the configuration of a main part of a connection structure according to Modification Example 5 of an embodiment of the present disclosure.

FIG. 7 is a partial cross-sectional view showing the configuration of a main part of a connection structure according to Modification Example 5 of the embodiment. In the Modification Example 5, in a control device 3C, a receptacle 36 is provided in the interior of the control device 3C, which is on the inside of a main body unit 35. That is, in a connection structure 600 according to the Modification Example 5, the connection portion between the plug 24 and the receptacle 36 is located in the interior of the control device 3C, which is on the inside of an opening 351 formed in the main body unit 35. In the Modification Example 5, since the outer casing 241 containing an electrically non-conductive magnetic material is located in a portion crossing the opening 351 of the main body unit 35, similar effects to the above embodiment can be obtained.

Figure 8:
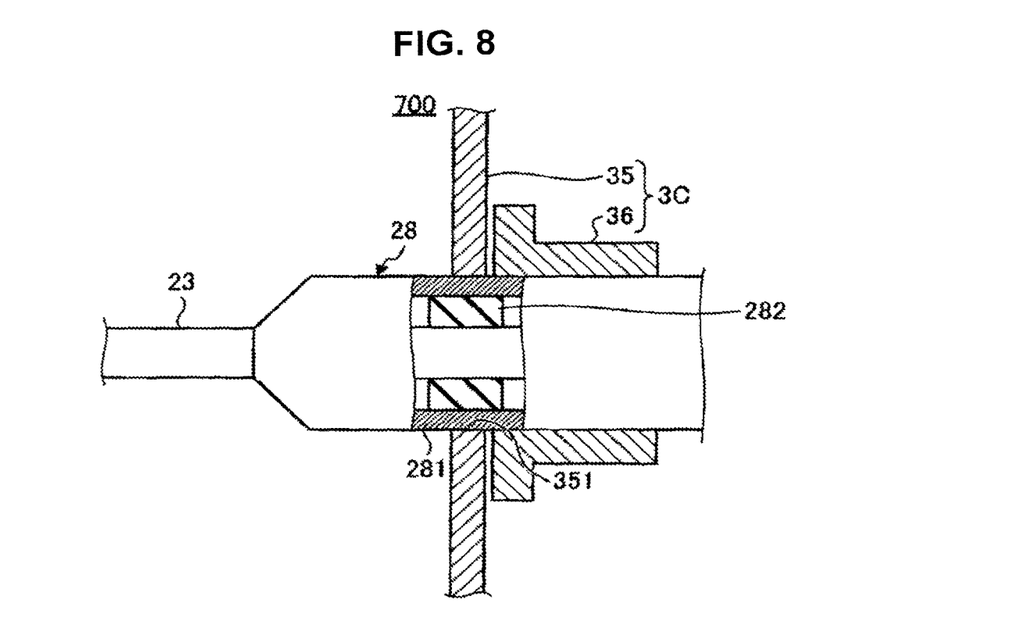
FIG. 8 is a partial cross-sectional view schematically showing the configuration of a main part of a connection structure according to Modification Example 6 of an embodiment of the present disclosure.

FIG. 8 is a partial cross-sectional view showing the configuration of a main part of a connection structure according to Modification Example 6 of the embodiment. A connection structure 700 shown in the drawing differs from the connection structure 600 described above in the configuration of the plug. Specifically, a plug 28 included in the connection structure 700 includes an outer casing 281 made of an electrically non-conductive resin and a circular cylindrical member 282 that is provided on the inner peripheral side of the outer casing 281 and is formed using an electrically non-conductive magnetic material. The circular cylindrical member 282 is provided in a position crossing the opening 351 of the main body unit 35 in a state where the plug 28 is inserted in the receptacle 36. In the Modification Example 6, since the circular cylindrical member 282 containing an electrically non-conductive magnetic material is located in a portion crossing the opening 351 of the main body unit 35, similar effects to the above embodiment can be obtained.

The combination of the plug and the receptacle is not limited to those described in the embodiment and Modification Examples 1 to 6, and any combination of the plug and the receptacle may be employed to the extent that it is a combination in which an electrically non-conductive magnetic material is located in a position crossing the opening of the main body unit of the control device in a state where the plug is inserted in the receptacle.

(Other Embodiments)

Hereinabove, embodiments of the present disclosure are described; but the present disclosure is not limited to the embodiments described above. For example, although in the root end-side device is configured as a control device in the connection structures described above, the root end-side device may be configured as a light source device. In this case, the plug receives a light guide. Further, in one medical device, any of the connection structures described above may be used for both of the connection structure between the endoscope and the control device and the connection structure between the endoscope and the light source device.

Figure 9:
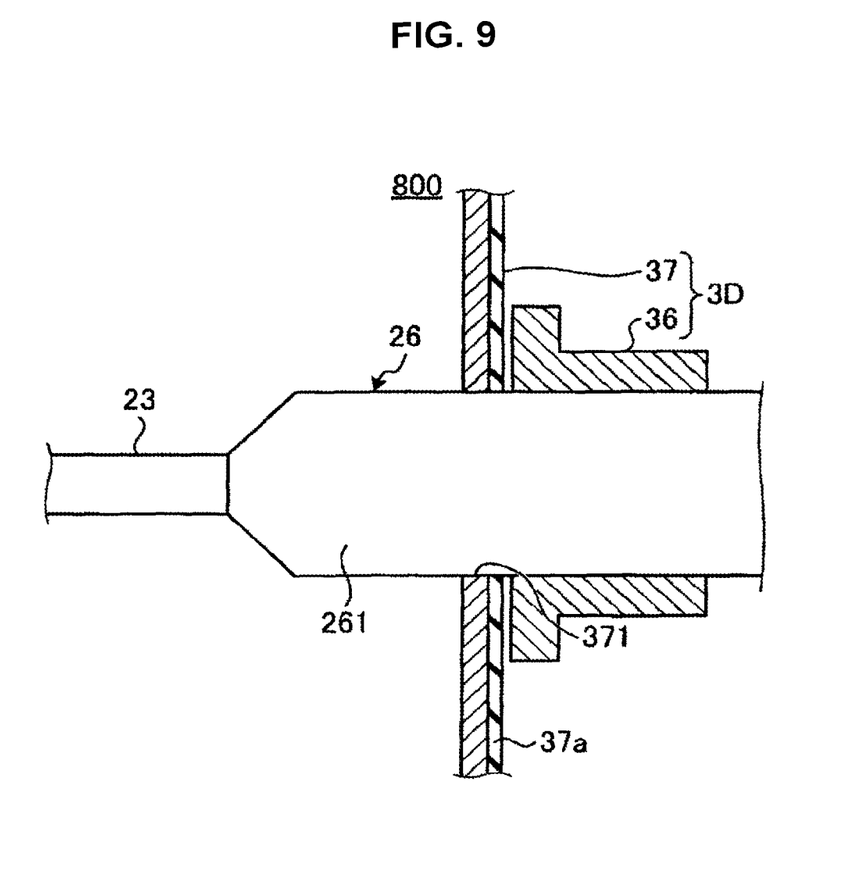
FIG. 9 is a partial cross-sectional view schematically showing the configuration of a main part of a connection structure according to another embodiment of the present disclosure.

FIG. 9 is a partial cross-sectional view showing the configuration of a main part of a connection structure according to another embodiment of the present disclosure. In the embodiment, an inner peripheral portion 37a made of an electrically non-conductive magnetic material is provided on the inner peripheral surface of a main body unit 37 of a control device 3D. Neither of the plug 26 and the receptacle 36 constituting a connection structure 800 contains an electrically non-conductive magnetic material. In this case, an electrically non-conductive magnetic material is provided on the side of the main body unit 37, as a portion crossing an opening 371 of the main body unit 37; thereby, similar effects to the above embodiment can be obtained. It is also possible to provide an electrically non-conductive magnetic material on the outer peripheral side of the main body unit. Further, it is also possible to provide a portion containing an electrically non-conductive magnetic material on the inner peripheral surface of the opening 351 formed in the main body unit 35 of the control device 3C described above (see FIG. 8). Further, any of the plugs 24, 27, and 28 described above may be used in place of the plug 26.

The present disclosure can be applied to all medical devices that are brought into contact with or inserted into an object to be observed and perform the observation etc. of the object to be observed. Examples of such a medical device include an ultrasonic diagnosis device and an X-ray device.

Additionally, the present technology may also be configured as below.

(1)

A connection structure for connecting a tip-side device and a root end-side device of a medical device, the medical device including the tip-side device configured to be brought into contact with or inserted into an object to be observed, and the root end-side device connected to the tip-side device and including a grounded outer casing, the connection structure including:

a plug provided at a root end of the tip-side device; and a receptacle provided in the root end-side device and configured to hold the plug by insertion, wherein at least one of the plug and the receptacle contains an electrically non-conductive magnetic material in a portion crossing an opening formed in the outer casing in a state where the plug is inserted in the receptacle.

(2)

The connection structure according to (1), wherein the magnetic material is provided in an outer casing of the plug.

(3)

The connection structure according to (1), wherein the magnetic material is provided on an inner peripheral side with respect to an outer casing of the plug.

(4)

The connection structure according to any one of (1) to (3), wherein the magnetic material is provided in the receptacle.

(5)
A medical device including:
the connection structure according to any one of (1) to (4).

(6)
The medical device according to (5),
wherein the tip-side device is an endoscope configured to be inserted into the object to be observed and acquire information of the object to be observed, and
the root end-side device is a control device configured to control the tip-side device and process information received from the tip-side device and/or a light source device configured to generate illumination light that the tip-side device applies to the object to be observed.

REFERENCE SIGNS LIST 1 endoscope system
2 endoscope
3, 3A, 3B, 3C, 3D control device
4 light source device
5 display device
21 insertion unit
23 cable
24, 26, 27, 28 plug
25 light guide
31, 35, 37 main body unit
32, 33, 34, 36 receptacle
34a, 37a, 271b inner peripheral portion
34b, 271a outer peripheral portion
100, 200, 300, 400, 500, 600, 700, 800 connection structure
241, 261, 271, 281 outer casing
242, 272 shield body
282 circular cylindrical member
311, 351, 371 opening

The invention claimed is:

1. A connection structure for connecting a tip-side device and a root end-side device of a medical device,
the medical device including:
the tip-side device including a patient circuit and configured to be brought into contact with or inserted into an object to be observed, and
the root end-side device connected to the tip-side device and including a grounded outer casing,
the connection structure comprising:
a plug provided at a root end of the tip-side device; and
a receptacle provided in the root end-side device and configured to hold the plug by insertion,
wherein at least one of the plug and the receptacle contains an electrically non-conductive magnetic material in a portion crossing an opening formed in the outer casing in a state where the plug is inserted in the receptacle, and the electrically non-conductive magnetic material is provided between the patient circuit and the grounded outer casing.

2. The connection structure according to claim 1, wherein the electrically non-conductive magnetic material is provided in an outer casing of the plug.

3. The correction structure according to claim 1, wherein the electrically non-conductive magnetic material is provided on an inner peripheral side with respect to an outer casing of the plug.

4. The connection structure according to claim 1, wherein the electrically non-conductive magnetic material is provided in the receptacle.

5. The connection structure according to claim 1, wherein the electrically non-conductive magnetic material is made of powdered magnetic material mixed with electrically non-conductive resin.

6. The connection structure according to claim 1, wherein the electrically non-conductive magnetic material is embodied in a cylindrical shape extending completely through the outer casing.

7. A medical device comprising:
a tip-side device including a patient circuit and configured to be brought into contact with or inserted into an object to be observed; and
a root end-side device connected to the tip-side device and including a grounded outer casing,
wherein a connection structure connecting the tip-side device and the root end-side device includes:
a plug provided at a root end of the tip-side device, and
a receptacle provided in the root end-side device and configured to hold the plug by insertion, and
at least one of the plug and the receptacle contains an electrically non-conductive magnetic material in a portion crossing an opening formed in the outer casing in a state where the plug is inserted in the receptacle, and the electrically non-conductive magnetic material is provided between the patient circuit and the grounded outer casing.

8. The medical device according to claim 7,
wherein the tip-side device is an endoscope configured to be inserted into the object to be observed and acquire information of the object to be observed, and
the root end-side device is a control device configured to control the tip-side device and process information received from the tip-side device and/or a light source device configured to generate illumination light that the tip-side device applies to the object to be observed.

9. The medical device according to claim 7, wherein the electrically non-conductive magnetic material is made of powdered magnetic material mixed with electrically non-conductive resin.

10. The medical device according to claim 7, wherein the electrically non-conductive magnetic material is embodied in a cylindrical shape extending completely through the outer casing.

11. A connection structure for connecting a tip-side device and a root end-side device of a medical device,
the medical device including:
the tip-side device including a patient circuit configured to be brought into contact with or inserted into an object to be observed, and
the root end-side device connected to the tip-side device and including an outer casing,
the connection structure comprising:
a plug provided at a root end of the tip-side device; and
a receptacle provided in the root end-side device and configured to hold the plug by insertion,
wherein an electrically non-conductive magnetic material is provided on a peripheral surface of the outer casing, and
wherein the patient circuit of the plug extends through an opening formed in the electrically non-conductive magnetic material in a state where the plug is inserted in the receptacle.

* * * * *